(12) United States Patent
Wainwright et al.

(10) Patent No.: US 7,901,899 B1
(45) Date of Patent: Mar. 8, 2011

(54) METHOD FOR CLASSIFYING A MICROORGANISM IN A BIOLOGICAL SAMPLE

(75) Inventors: Norman R. Wainwright, Johns Island, SC (US); Dana M. Nutter, Charleston, SC (US)

(73) Assignee: Charles River Laboratories, Inc., Wilmington, MA (US)

( * ) Notice: Subject to any disclaimer, the term of this patent is extended or adjusted under 35 U.S.C. 154(b) by 0 days.

(21) Appl. No.: 12/257,030

(22) Filed: Oct. 23, 2008

Related U.S. Application Data

(63) Continuation of application No. 11/331,600, filed on Jan. 13, 2006, now Pat. No. 7,479,375.

(60) Provisional application No. 60/643,697, filed on Jan. 13, 2005.

(51) Int. Cl.
*G01N 33/53* (2006.01)

(52) U.S. Cl. ........................................ 435/7.2

(58) Field of Classification Search .................. None
See application file for complete search history.

(56) References Cited

U.S. PATENT DOCUMENTS

| | | |
|---|---|---|
| 3,915,805 A | 10/1975 | Levin |
| 3,944,391 A | 3/1976 | Harris et al. |
| 3,954,663 A | 5/1976 | Yamamoto et al. |
| 4,038,029 A | 7/1977 | Teller et al. |
| 4,038,147 A | 7/1977 | Reno |
| 4,221,865 A | 9/1980 | Dubczak et al. |
| 4,221,866 A | 9/1980 | Cotter |
| 4,245,044 A | 1/1981 | Kuo et al. |
| D258,144 S | 2/1981 | Kallet et al. |
| 4,273,557 A | 6/1981 | Juranas |
| 4,279,774 A | 7/1981 | Lindsay et al. |
| 4,301,245 A | 11/1981 | Lindsay et al. |
| 4,322,217 A | 3/1982 | Dikeman |
| 4,370,413 A | 1/1983 | Neeman et al. |
| 4,376,819 A | 3/1983 | Brown et al. |
| D278,182 S | 3/1985 | Aihara et al. |
| 4,606,824 A | 8/1986 | Chu et al. |
| 4,619,530 A * | 10/1986 | Meserol et al. ............... 356/440 |
| 4,717,658 A | 1/1988 | Michaels |
| 4,806,316 A | 2/1989 | Johnson et al. |
| D325,090 S | 3/1992 | Karp et al. |
| D330,428 S | 10/1992 | Lewis et al. |
| 5,155,032 A | 10/1992 | Tanaka et al. |
| 5,179,006 A | 1/1993 | Matuura et al. |
| 5,266,461 A | 11/1993 | Tanaka |
| D342,793 S | 12/1993 | Balmer |
| D343,905 S | 2/1994 | Nagata et al. |
| 5,286,625 A | 2/1994 | Tanaka et al. |
| 5,310,657 A | 5/1994 | Berzofsky |
| 5,316,911 A | 5/1994 | Baek et al. |
| 5,318,893 A | 6/1994 | Matuura et al. |
| D353,676 S | 12/1994 | Kelln et al. |
| 5,372,946 A | 12/1994 | Cusak et al. |
| 5,389,547 A | 2/1995 | Tanaka et al. |
| 5,401,647 A | 3/1995 | Tanaka et al. |
| 5,474,984 A | 12/1995 | Tanaka et al. |
| 5,504,011 A | 4/1996 | Gavin et al. |
| 5,518,006 A | 5/1996 | Mawhirt et al. |
| 5,534,226 A | 7/1996 | Gavin et al. |
| 5,550,030 A | 8/1996 | Tanaka et al. |
| 5,574,023 A | 11/1996 | Shibata et al. |
| 5,591,403 A | 1/1997 | Gavin et al. |
| 5,591,628 A | 1/1997 | Bæk et al. |
| 5,605,806 A | 2/1997 | Tanaka et al. |
| 5,637,474 A | 6/1997 | Takaoka et al. |
| D380,555 S | 7/1997 | Kurosaki et al. |
| 5,681,710 A | 10/1997 | Tanaka et al. |
| 5,695,948 A | 12/1997 | Tanaka et al. |
| 5,702,882 A | 12/1997 | Tamura et al. |
| D390,661 S | 2/1998 | Foggia |
| D391,373 S | 2/1998 | Shartle |
| 5,731,212 A | 3/1998 | Gavin et al. |
| 5,750,500 A | 5/1998 | Tsuchiya et al. |
| 5,795,962 A | 8/1998 | Iwanaga et al. |
| 5,800,781 A | 9/1998 | Gavin et al. |
| 5,836,360 A | 11/1998 | Gavin et al. |
| 6,046,021 A | 4/2000 | Bochner |
| D437,419 S | 2/2001 | Kraack et al. |
| D445,909 S | 7/2001 | Pogorzelski |

(Continued)

FOREIGN PATENT DOCUMENTS

EP 0121868 10/1984

(Continued)

OTHER PUBLICATIONS

Gomez-Jimenez, et al. "L-arginine: nitric oxide pathway in endotoxemia and human septic shock", Critical Care Medicine, 1995, 23(2):253-258.*

Aono et al., (1996) "Interaction Between Hemocytes and Plasma is Necessary for Hemolymph Coagulation in the Spiny Lobster, *Panulirus japonicus*," Comp. Biochem. Physiol. 113A(3):301-305.

Asokan et al., (1997) "Activation of Prophenoloxidase in the Plasma and Haemocytes of the Marine Mussel *Perna viridis Linnaeus*," Developmental and Comparative Immunology, 21(1):1-12.

Aspan et al., (1995) "cDNA Cloning of Prophenoloxidase from the Freshwater Crayfish *Pacifastacus leniusculus* and Its Activation," Proc. Nat'l Acad. Sci. USA, 92:939-943.

(Continued)

*Primary Examiner* — Jon P Weber
*Assistant Examiner* — Bin Shen
(74) *Attorney, Agent, or Firm* — Goodwin Procter LLP

(57) ABSTRACT

The invention provides a method using a hemocyte preparation, for example, *Limulus* amebocyte lysate, for detecting in a single assay the presence of at least one of a Gram negative bacterium, a Gram positive bacterium, and a fungus in a sample of interest. The method exploits the differential reactivity of Gram negative bacteria, Gram positive bacteria, and fungi with the hemocyte preparation to produce measurable changes in a property, for example, an optical property, of the mixture. Because the Gram negative bacteria, Gram positive bacteria and fungi each produce different changes in a given property, for example, an optical property, it is possible to classify the type of microorganism present in the sample of interest.

16 Claims, 5 Drawing Sheets

U.S. PATENT DOCUMENTS

| | | | |
|---|---|---|---|
| 6,270,982 | B1 | 8/2001 | Jordan et al. |
| 6,303,389 | B1 | 10/2001 | Levin et al. |
| 6,306,659 | B1 | 10/2001 | Parce et al. |
| 6,391,570 | B1 | 5/2002 | Jordan et al. |
| 6,428,971 | B1 | 8/2002 | Shinabarger et al. |
| 6,440,722 | B1 | 8/2002 | Knapp et al. |
| D463,570 | S | 9/2002 | Bedingham et al. |
| 6,451,610 | B1 | 9/2002 | Gorman et al. |
| D472,324 | S | 3/2003 | Rumore et al. |
| 6,696,261 | B2 | 2/2004 | Patel et al. |
| 7,329,538 | B2 | 2/2008 | Wainwright et al. |
| 7,479,375 | B2 | 1/2009 | Wainwright et al. |
| 2003/0104501 | A1 | 6/2003 | Jordan et al. |
| 2004/0241788 | A1 | 12/2004 | Wainwright et al. |
| 2006/0183181 | A1 | 8/2006 | Wainwright et al. |
| 2006/0216780 | A1 | 9/2006 | Wainwright et al. |
| 2008/0020422 | A1 | 1/2008 | Wainwright et al. |

FOREIGN PATENT DOCUMENTS

| | | |
|---|---|---|
| EP | 0816513 | 1/1998 |
| GB | A2080524 | 2/1982 |
| JP | 61093958 | 5/1986 |
| WO | WO-8302123 | 6/1983 |
| WO | WO-9919355 | 4/1999 |
| WO | WO-9953322 | 10/1999 |
| WO | WO-2005010207 | 2/2005 |
| WO | WO-2006076617 | 7/2006 |
| WO | WO-2007078268 | 7/2007 |

OTHER PUBLICATIONS

Aspan et al., (1990) "The Effect of Endogeneous Proteinase Inhibitors on the Prophenoloxidase Activating Enzyme, A Serine Proteinase from Crayfish Haemocytes," Insect Biochem, 20(5):485-492.

Bettencourt et al., (2004) "Hemolymph-Dependent and Independent Responses in *Drosophila* Immune Tissue," Journal of Cellular Biochemistry, 92:849-863.

Bullis, "Invertebrate Pathology: Responses to Injury and Disease," Aquavet II, Comparative Pathology of Aquatic Animals, Laboratory for Marine Animal Health, School of Veterinary Medicine, University of Pennsylvania, undated.

Burmester et al., (2002) "Origin and Evolution of Arthropod Hemocyanins and Related Proteins," J Comp Physiol B 172:95-107.

Charles River Laboratories, (2002) "In Vitro Pyrogen Test (IPT)."

Charles River Laboratories, (2002) "IPT Assay Steps."

"Comparative Immunology," Department of Comparative Physiology—Uppsala University, http://www.jamfys.ebc.uu.se/propo.html, printed May 22, 2002.

Cooper et al. (1997) "The Impact of Non-endotoxin LAL-Reactive Materials on *Limulus* Amebocyte Lysate Analyses," PDA Journal of Pharmaceutical Science & Technology, 51(1):2-6.

Datta et al., (1989) "Purification of a Unique Glycoprotein that Enhances Phenol Oxidase Activity in Scorpion (*Heterometrus bengalensis*) Haemolymph," Biochem. J. 260:525-529.

Decker, et al., (2001) "SDS-Induced Phenoloxidase Activity of Hemocyanins from *Limulus polyphemus, Eurypelma californicum* and *Cancer Magister*," The Journal of Biological Chemistry, 276(21):17796-17799.

Decker, et al., (1998) "Tarantula Hemocyanin Shows Phenoloxidase Activity," The Journal of Biological Chemistry, 279(40):25889-25892.

De Kimpe et al., (1995) "The Cell Wall Components Peptidoglycan and Lipoteichoic Acid from *Staphylococcus aureus* Act in Synergy to Cause Shock and Multiple Organ Failure," Medical Sciences, pp. 10359-10363.

Duner, Kristina I., (1993) "A New Kinetic Single-Stage *Limulus* Amoebycyte Lysate Method for the Detection of Endotoxin in Water and Plasma," Journal of Biochemical and Biophysical Methods, 26:131-142.

Gollas-Galvan et al, (1999) "Prophenoloxidase from Brown Shrimp (*Penaeus californiensis*) Hemocytes," Comparative Biochemistry and Physiology Part B, 122:77-82.

Ganguly et al., (1985) "Tyrosine Phosphorylation of a 94-kDa Protein of Human Fibroblasts Stimulated by Streptococcal Lipoteichoic Acid," The Journal of Biological Chemistry, 260(24):13342-13346.

Geng et al., (1998) "Hemostatis in Larvae of *Manduca sexta*: Formation of a Fibrous Coagulum by Hemolymph Proteins," Biochemical and Biophysical Research Communications, 155(2):1060-1065.

Ginsburg, (2002) "Role of Lipoteichoic Acid in Infection and Inflammation," The Lancet Infectious Diseases, 2:171-179.

Goldsworthy et al., (2002) "Adipokinetic Hormone Enhances Laminarin and Bacterial Lipopolysaccharide-Induced Activation of the Prophenoloxidase Cascade in the African Migratory Locust," *Locusta migratoria*, Journal of Insect Physiology, 48:601-608.

Halwani et al., (2000) "Apolipophorin-III and the Interactions of Lipoteichoic Acids with the Immediate Immune Responses of *Galleria mellonella*," Journal of Invertebrate Pathology, 76:233-241.

Hamada et al., (1985) "Chemical Properties and Immunobiological Activities of Streptococcal Lipoteichoic Acids," Zbl. Bakt. Hyg. A 259:228-243.

Harrington et al., (1995) "Synthesis of Peptidoglycan and Teichoic Acid in *Bacillus subtilis*: Role of the Electrochemical Proton Gradient," Journal of Bacteriology, 159(3):925-933.

Hauton et al., (1995) "Circatidal Rhythmicity in the Activity of the Phenoloxidase Enzyme in the Common Shore Crab, *Carcinus maenas*," Comp. Biochem. Physiol. 111 B(3):347-352.

Hauton et al., (1997) "In Situ Variability in Phenoloxidase Activity in the Shore Crab, *Carcinus maenas* (L.)," Comp. Biochem. Physiol. 117B(2):267-271.

Hernandez-Lopez et al., (2003) "In the Spiny Lobster (*Panulirus interruptus*) the Prophenoloxidase is Located in Plasma not in Haemocytes," Fish & Shellfish Immunology, 14:105-114.

Hurley, James C., (1995) "Endotoxemia: Methods of Detection and Clinical Correlates," Clinical Microbiology Reviews, 8(2):268-292.

Iwanaga et al., (1978) "Chromogenic Substrates for Horseshoe Crab Clotting Enzyme: Its Application for the Assay of Bacterial Endotoxins," Hemostasis, Chapter 7:183-188.

Iwanaga Sadaaki, (1993) "The *Limulus* Clotting Reaction," Current Opinion in Immunology, Current Biology Ltd., 5(5):74-82.

Iwanaga, (2002) "The Molecular Basis of Innate Immunity in the Horseshoe Crab," Curr Opin Immunol, 14:87-95.

Jiang et al., (1997) "Characterization and Functional Analysis of 12 Naturally Occurring Reactive Site Variants of Serpin-1 from *Manduca sexta*," The American Society for Biochemistry and Molecular Biology, Inc., 272(2):1082-1087.

Jiang et al., (1998) "Pro-Phenol Oxidase Activating Proteinase from an Insect, *Manduca sexta*: A Bacteria-Inducible Protein Similar to *Drosophila easter*," Proc. Natl. Acad. Sci. USA, 95(21):12220-12225, Biochemistry.

Jiang et al., (2004) "β-1, 3-Glucan Recognition Protein-2 ((βGRP-2) from *Manduca sexta*: an Acute-phase Protein that Binds (β-1, 3-Glucan and Lipoteichoic Acid to Aggregate Fungi and Bacteria and Stimulate Prophenoloxidase Activation," InsectBiochemistry and Molecular Biology, vol. 34, Issue 1, pp. 89-100 (2004).

Johansson et al., (1989) "Cellular Immunity in Crustaceans and the proPO System," Parasitology Today, 5(6):171-176.

Jolliffe et al., (1981) "The Energized Membrane and Cellular Autolysis in *Bacilluls subtillis*," Cell, 25:753-763.

Kawabata et al., (1996) "The Clotting Cascade and Defense Molecules Found in the Hemolymph of the Horseshoe Crab," New Directions in Invertebrate Immunology, 255-283.

Kobayashi et al., (2000) "Detection of Peptidoglycan in Human Plasma Using the Silkworm Larvae Plasma Test," FEMS Immunology and Medical Microbiology, 28:49-53.

Lackie et al., (1980) "Invertebrate Immunity," Parasitology, 80:393-412.

Lokor et al., (1994) "On Being a Parasite in an Invertebrate Host: A Short Survival Course," J. Parasitol., 80(5):728-747.

Mattsson et al., (2004) "Highly Purified Lipoteichoic Acid from *Staphylococcus aureus* Induces Procoagulant Activity and Tissue Factor Expression in Human Monocytes but is a Weak Inducer in Whole Blood: Comparison with Peptidoglycan," Infection andImmunity, 72(7):4322-6.

Morath et al.,(2002) "Structural Decomposition and Heterogeneity of Commercial Lipoteichoic Acid Preparations," Infection and Immunity, 70(2):938-944.

Muta et al., (1991) "Limuls Factor C," Journal of Biological Chemistry, American Society of Biological Chemists-Baltimore, MD, 266(10):6554-6561.

Nagai et al., (2000) "A Link Between Blood Coagulation and Prophenol Oxidase Activation in Arthropod Host Defense," The Journal of Biological Chemistry, 275(38):29264-29267.

Nagai et al., (2001) "Functional Conversion of Hemocyanin to Phenoloxidase by Horseshoe Crab Antimicrobial Peptides," The Journal of Biological Chemistry, 276(29):27166-27170.

Nellaiappan et al., (1996) "On the Presence of Prophenoloxidase in the Hemolymph of the Horseshoe Crab, *Limulus*," Comp. Biochyem. Physiol., 113B(1):163-168.

Obayashi et al., (1985) "A new chromogenic endotoxin-specific assay using recombined *Limulus* coagulation enzymes and its clinical applications," Clin. Chin. Acta 149:55-65.

Parrinello et al., (2003) "Phenoloxidase in Ascidian Hemocytes: Characterization of the Pro-Phenoloxidase Activating System," Comparative Biochemistry and Physiology Park B: Biochemistry and Molecular Biology, 135(4):583-591.

Pearson et al, (1984) "Comparison of Chemical Analyses of Hollow-Fiber Dialyzer Extracts," Artificial Organs, 8(3):291-298.

Ratcliffe et al., (1991) "Activation of the Prophenoloxidase Cascade and Initiation of Nodule Formation in Locusts by Bacterial Lipopolysaccharides," Developmental and Comparative Immunology, 15:33-39.

Roslansky et al., (1991) "Sensitivity of *Limulus* Amebocyte Lysate (LAL) to LAL-Reactive Glucans," J. Of Clinical Microbiology, 29(11):2477-2483.

Saul et al., (1987) "The Majority of Prophenoloxidase in the Hemolymph of *Manduca sexta* is Present in the Plasma and Not in the Hemocytes," Developmental and Comparative Immunology, 11:479-485.

Seki et al., (1994) "Horseshoe Crab (1,3)-β-D-Glucan-sensitive Coagulation Factor G," J. Of Biological Chem. 269:1370-1374.

Shah et al., (2004) "A Novel Glucan-Binding Protein with Lipase Activity from the Oral Pathogen *Streptococcus mutans*," Microbiology, 150:1947-1956.

Soderhall, (1982) "Prophenoloxidase Activating System and Melanization—A Recognition Mechanism of Arthropods? A Review," Developmental and Comparative Immunology, 6:601-611.

Soderhall et al., (1994) "The Prophenoloxidase Activating System and its Role in Invertebrate Defence," Annals of the New York Academy of Sciences, 712:155-161.

Soderhall et al., (1986) "Chapter 15 The Prophenoloxidase Activating System: The Biochemistry of its Activation and Role in Arthropod Cellular Immunity, with Special Reference to Crustaceans," Immunity in Invertebrates, pp. 208-223 (1986).

Sritunyalucksana et al., (2001) "Peroxnectin, a Cell Adhesive Protein Associated with the proPO System from the Black Tiger Shrimp, *Penaeus monodon*," Developmental and Comparative Immunology, 25:353-363.

Sugumaran et al., (1991) "Lysolecithin—A Potent Activator of Prophenoloxidase from the Hemolymph of the Lobster, *Homarus americanas*," Biochemical and Biophysical Research Communications, 176(3):1371-1376.

Tarsi-Tsuk et al., (1990) "Stimulation of the Respiratory Burst in Peripheral Blood Monocytes by Lipoteichoic Acid," The Journal of Immunology, 144(7):2665-2670.

"The Horseshoe Crab," http://www.horseshoecrab.org/anat/anat.html, printed Aug. 6, 2002.

"The Prophenoloxidase (proPO) Activation System," http://sbs.umkc.edu/yux/PPO%20activation.html, printed Apr. 16, 2003.

Tsuchiya et al., (1996) "Detection of Peptidoglycan and β-Glucan with Silkworm Larvae Plasma Test," FEMS Immunology and Medical Microbiology, 15:129-134.

Tsuji et al., (1984) "Automation of Chromogenic Substrate *Limulus* Amebocyte Lystate Assay Method of Endotoxin by Robotic System," Applied and Environmental Microbiology, 48(3):550-555.

Vargas-Albores et al, (1993) "An Anticoagulant Solution for Haemolymph Collection and Prophenoloxidase Studies of Penaeid Shrimp (*Penaeus californiensis*)," Comp. Biochem. Physiol, 106A(2):299-303.

Wilson et al., (1986) "Identity of *Limulus* Amoebycyte Lysate-Active Root Surface Materials from Periodontally Involved Teeth," Journal of Clinical Periodontology, 13(8):743-747.

Patent Cooperation Treaty (PCT) International Search Report; International Application No. PCT/US98/20823; mailed Mar. 3, 1999.

Patent Cooperation Treaty (PCT) IPER; International Application No. PCT/US98/20823, mailed Jan. 24, 2000.

Patent Cooperation Treaty (PCT) Invitation to Pay Additional Fees and Partial International Search; International Application No. PCT/US04/008013; mailed Dec. 10, 2004.

"The proPO-system," Department of Comparative Physiology, Uppsala University, available at http://www.jamfys.ebc.uu.se/propo.html, printed May 22, 2002.

Decker et al., (2004) "Recent Findings on Phenoloxidase Activity and Antimicrobial Activity of Hemocyanins," Developmental & Comparative Immunology, 28:673-687.

Patent Cooperation Treaty (PCT) International Search Report; International Application No. PCT/US2004/008013, mailed on Apr. 8, 2005.

Patent Cooperation Treaty (PCT) Written Opinion of the International Searching Authority for PCT Application No. PCT/US2004/008013, mailed on Apr. 8, 2005.

Coates, D.A., (1977) "Enhancement of the Sensitivity of the *Limulus* Assay for the Detection of Gram Negative Bacteria," Journal of Applied Bacteriology 42:445-449.

Inada et al., (2003) "A Silkworm Larvae Plasma Test for Detecting Peptidoglycan in Cerebrospinal Fluid is Useful for the Diagnosis of Bacterial Meningitis," Microbiology and Immunology, 47:(10):701-707.

Janda et al., (1971) "A Colorimetric Estimation of Lipopolysaccharides," Febs Letters 16(4):343-345.

Maeda, M. et al., (1979) "Chromogenic Assay Method of Lipopolysaccharide (LPS) for Evaluating Bacterial Standing Crop in Seawater," Journal of Applied Bacteriology 47:175-182.

Sigma Chemical Company E-Toxate Technical Bulletin (2000) No. 210: 1-4.

Wiegel, J. et al.,(1982) "Determination of the Gram Type Using the Reaction Between Polymyxin B and Lipopolysaccarides of the Outer Cell Wall of Whole Bacteria," Journal of General Microbiology 128:2261-2270.

Charles River Laboratories, (2001) "LAL Products and Services".

Prior, Richard B. Ed., (1990) "Clinical Applications of the *Limulus* Amebocyte Lysate Test" CRC Press, pp. 28-36.

Patent Cooperation Treaty (PCT) International Search Report; International Application No. PCT/US2006/001305, completed on Jul. 18, 2006.

Patent Cooperation Treaty (PCT) International Search Report; International Application No. PCT/US2005/043426, completed Jul. 18, 2007 and mailed Aug. 9, 2007 (4 pages).

Armstrong et al. (1982) "Endotoxin-Induced Degranulation of the *Limulus* Amebocyte," Experimental Cell Research 140:15-24.

Johansson et al. (1985) "Exocytosis of the Prophenoloxidase Activating System from Crayfish Haemocytes," J Comp Physiol B 156:175-181.

Hausmann et al. (2002) "Gel clot LAL assay in the initial management of peritoneal dialysis patients with peritonitis: a retrospective study," Nephrology Dialysis Transplantation, 15:680-683.

Mottar et al. (1993) "Routine *Limulus* amoebocyte lysate (LAL) test for endotoxin determination in milk using a Toxinometer ET-201", Journal of Dairy Research, 60:223-228.

Roth et al. (1989) "A modified *Limulus* amebocyte lysate test with increased sensitivity for detection of bacterial endotoxin", J Lab Clin Med, 114(3):306-311.

Ho, B., et al., (1993) "Electrophoretic Analysis of Endotoxin-Activated Gelation Reaction of *Carcinoscorpius rotundicauda* Amoebocyte Lysate," Biochemistry and Molecular Biology International, 29(4): 687-694.

Iwanaga, S., et al., (1986) "The Hemolymph Coagulation System in Invertebrate Animals," Journal of Protein Chemistry, 5(4): 255-268.

Levin, J. and Bang, F.B., (1968) "Clottable Protein in *Limulus*: Its Localization and Kinetics of Its Coagulation by Endotoxin," Thromb. Diath. Haemorrh., 19(1): 186-197.

Morita, T., et al., (1981) "A New (1→3)-β-D-Glucan-Mediated Coagulation Pathway Found in *Limulus* Amebocytes," FEBS Letters, 129(2): 318-321.

Muta, T., et al., (1987) "Primary Structure of Anti-Lipopolysaccharide Factor from American Horseshoe Crab, *Limulus polyphemus*," J. Biochem, 101(6): 1321-1330.

Nakamura, T., et al., (1986) "Lipopolysaccharide-Sensitive Serine-Protease Zymogen (Factor C) Found in *Limulus* Hemocytes," Eur. J. Biochemistry, 154: 511-521.

Devleeschouwer, M. J., et al., (1985) "Studies on the Sensitivity and Specificity of the *Limulus* Amebocyte Lysate Test and Rabbit Pyrogen Assays," Appl. Environ. Microbiol., 50(6):1509-1511.

* cited by examiner

METHOD FOR CLASSIFYING A MICROORGANISM IN A BIOLOGICAL SAMPLE

RELATED APPLICATIONS

This application is a continuation application of U.S. patent application Ser. No. 11/331,600, filed Jan. 13, 2006, which claims the benefit of and priority to U.S. Patent Application Ser. No. 60/643,697, filed Jan. 13, 2005, the disclosure of each is incorporated by reference herein.

FIELD OF THE INVENTION

The present invention relates generally to a method for classifying a microorganism in a test sample. More particularly, the invention relates to a method using a hemocyte preparation for classifying microorganisms, for example, Gram positive bacteria, Gram negative bacteria, and fungi, in the test sample.

BACKGROUND OF THE INVENTION

Microbial contamination by, for example, Gram positive bacteria, Gram negative bacteria, and fungi, for example, yeasts and molds, may cause severe illness and, in some cases, even death in humans. Manufacturers in certain industries, for example, the pharmaceutical, medical device, water, and food industries, must meet exacting standards to verify that their products do not contain levels of microbial contaminants that would otherwise compromise the health of a recipient. These industries require frequent, accurate, and sensitive testing for the presence of such microbial contaminants to meet certain standards, for example, standards imposed by the United States Food and Drug Administration (USFDA) or Environmental Protection Agency. By way of example, the USFDA requires certain manufacturers of pharmaceuticals and invasive medical devices to establish that their products are free of detectable levels of Gram negative bacterial endotoxin.

To date, a variety of assays have been developed to detect the presence and/or amount of a microbial contaminants in a test sample. One family of assays use hemocyte preparations derived from the hemolymph of crustaceans, for example, horseshoe crabs. These assays typically exploit, in one way or another, a clotting cascade that occurs when the hemocyte lysate is exposed to a microbial contaminant. For example, FIG. 1 shows a schematic representation of certain clotting cascades known to be present in hemocyte lysate produced from the hemolymph of the horseshoe crab, *Limulus polyphemus*. Such lysates are known in the art as *Limulus* amebocyte lysate or LAL.

As shown in FIG. 1, the coagulation system of LAL, like the mammalian blood coagulation system, comprises at least two coagulation cascades that include an endotoxin or lipopolysaccharide (LPS) mediated pathway (the Factor C pathway) and a $(1\rightarrow3)$-$\beta$-D glucan mediated pathway (the Factor G pathway). See, for example, Morita et al. (1981) FEBS LETT. 129: 318-321 and Iwanaga et al. (1986) J. PROTEIN CHEM. 5: 255-268.

It is understood that Gram negative bacteria can be detected using LAL based assays. For example, Gram negative bacteria produce endotoxin or LPS, which after binding to LPS binding protein activates the Factor C pathway in LAL (see, FIG. 1). The endotoxin or LPS-mediated activation of LAL has been thoroughly documented in the art. See, for example, Levin et al. (1968) THROMB. DIATH. HAEMORRH. 19: 186; Nakamura et al. (1986) EUR. J. BIOCHEM. 154: 511; Muta et al. (1987) J. BIOCHEM. 101: 1321; and Ho et al. (1993) BIOCHEM. & MOL. BIOL. INT. 29: 687. When bacterial endotoxin is contacted with LAL, the endotoxin initiates a series of enzymatic reactions, known as the Factor C pathway, that are understood to involve three serine protease zymogens called Factor C, Factor B, and pro-clotting enzyme (see, FIG. 1). Briefly, upon exposure to endotoxin, the endotoxin-sensitive factor, Factor C, is activated. Activated Factor C thereafter hydrolyses and activates Factor B, whereupon activated Factor B activates proclotting enzyme to produce clotting enzyme. The clotting enzyme thereafter hydrolyzes specific sites, for example, $Arg^{18}$-$Thr^{19}$ and $Arg^{46}$-$Gly^{47}$ of coagulogen, an invertebrate, fibrinogen-like clottable protein, to produce a coagulin gel. See, for example, U.S. Pat. No. 5,605,806.

Furthermore, it is also understood that $(1\rightarrow3)$-$\beta$-D glucans and other LAL-reactive glucans, produced by fungi, for example, yeasts and molds, can also activate the clotting cascade of LAL, through a different enzymatic pathway known as the Factor G pathway (see, FIG. 1). It is understood that Factor G is a serine protease zymogen that becomes activated by $(1\rightarrow3)$-$\beta$-D glucan or other LAL reactive glucans. Upon exposure to $(1\rightarrow3)$-$\beta$-D glucan, for example, Factor G is activated to produce activated Factor G. It is understood that activated Factor G thereafter converts the proclotting enzyme into clotting enzyme, whereupon the clotting enzyme converts coagulogen into coagulin.

Although the detection of bacterial and fungal contamination can be extremely important, the ability to discriminate between these different organisms can provide useful information about an infectious agent causing an infection in an individual or the source and type of contamination present in a test sample. For example, once an infectious agent has been identified, a physician can then prescribe the most appropriate medication for treating an infection. Furthermore, once the type of bacterial or fungal contamination has been identified, then this type of information may speed up the process of identifying the source of contamination in, for example, a water supply. As a result, once the source of contamination has been identified, further contamination can be mitigated. However, there is still an ongoing need for a simple, routine method that in a single assay can distinguish between Gram negative bacteria, Gram positive bacteria, and fungi in a sample of interest.

SUMMARY OF THE INVENTION

The invention is based, in part, upon the discovery that it is possible to use a hemocyte preparation in a single, routine assay that can classify a microorganism present in a biological sample. In other words, the method of the invention permits one to determine whether microbes isolated from a sample of interest are a Gram negative bacterium, a Gram positive bacterium, or a fungus.

In one aspect, the invention provides a method of classifying a microorganism present in a test sample. The method comprises the steps of: (a) combining the sample to be tested with a hemocyte preparation to produce a mixture; (b) measuring either (i) an optical property of the mixture at a preselected time or (ii) a time in which a preselected change occurs in an optical property of the mixture; and (c) comparing the optical property of step (b)(i) or the time value of step (b)(ii) with one or more (for example, two or three) standard values to determine whether the sample contains a Gram negative bacterium, a Gram positive bacterium, or a fungus, for example, a yeast or a mold.

The optical property measured in step (b)(i) can be the absorbance of light at a preselected wavelength. Alternatively, the optical property measured in step (b)(i) can be the transmittance of light at a preselected wavelength. Alternatively, the optical property measured in step (b)(i) can be the turbidity of the sample. In this method, a first standard value of the optical property is indicative of the presence of a Gram negative bacterium in the sample. A second standard value of the optical property is indicative of the presence of a fungus in the sample. A third standard value of the optical property is indicative of the presence of a Gram positive bacterium in the sample. Each standard value may comprise a range of a given optical property indicative, for example, of a Gram negative bacterium, a Gram positive bacterium, or a fungus.

The optical property measured in step (b)(ii) can be the absorbance of light at a preselected wavelength. Alternatively, the optical property measured in step (b)(ii) can be the transmittance of light at a preselected wavelength. Alternatively, the optical property measured in step (b)(ii) can be the turbidity of the sample. In this method, a first standard value of time is indicative of the presence of a Gram negative bacterium in the sample. A second standard value of time is indicative of the presence of a fungus in the sample. A third standard value of time value is indicative of the presence of a Gram positive bacterium in the sample. Each standard value of time may comprise a range of times indicative, for example, of a Gram negative bacterium, a Gram positive bacterium, or a fungus.

The presence of each type of organism can be analyzed in separate individual assays or in a combined assay. For example, the assay may detect (i) Gram positive bacteria, (ii) Gram negative bacteria, (iii) fungus, (iv) a combination of Gram negative bacteria and Gram positive bacteria, (v) a combination of Gram negative bacteria and fungus, (vi) a combination of Gram positive bacteria and fungus, and (vii) a combination of Gram negative bacteria, Gram positive bacteria and fungus.

A hemocyte preparation useful in step (a) can be an amebocyte lysate, for example, a *Limulus* amebocyte lysate. Furthermore, depending upon the assay to be performed, in step (a) the mixture may further comprise a chromogenic substrate. By way of example, the chromogenic substrate can comprise a para-nitroaniline chromophore. Also, by way of example, the chromogenic substrate can comprise Ile-Glu-Ala-Arg-pNA (SEQ ID NO: 1), where pNA is a para-nitroaniline group.

It is understood that the method of the invention can be facilitated using a variety of kinetic or endpoint assays. Exemplary endpoint assays include an endpoint chromogenic assay and an endpoint turbidimetric assay. Exemplary kinetic assays include a one-step kinetic assay, a multi-step kinetic assay, and a kinetic turbidimetric assay. It is understood that the foregoing assays may be performed either in a cartridge or in a well defined by a solid support.

The foregoing and other objects, features and advantages of the present invention will be made more apparent from the following drawings and detailed description of preferred embodiments of the invention.

BRIEF DESCRIPTION OF THE DRAWINGS

The objects and features of the invention may be better understood by reference to the drawings described below in which.

FIGS. 4A-4D are schematic illustrations of an exemplary cartridge in which FIG. 4A is a view of a bottom half of an exemplary cartridge of the invention showing the locations of immobilized hemocyte preparation and chromogenic substrate, FIG. 4B is a view of a top half of an exemplary cartridge of the invention, FIG. 4C is a cross-sectional view of the fabricated cartridge through section A-A', and FIG. 4D is a cross-sectional view of the fabricated cartridge through section B-B'.

In the drawings, which are not necessarily drawn to scale, like characters refer to the same or similar parts throughout the Figures.

DETAILED DESCRIPTION OF THE INVENTION

Figure 1:
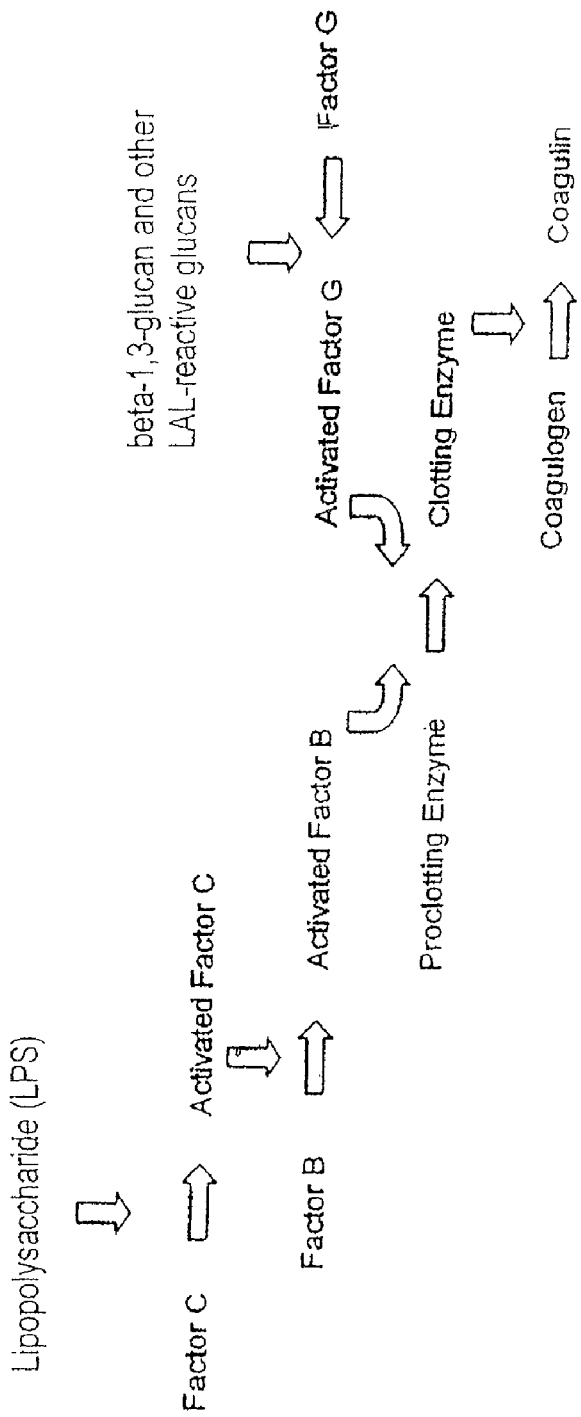
FIG. 1 is a schematic representation of the Factor C and Factor G cascades present in *Limulus* amebocyte lysate.

The invention is based, in part, upon the discovery that it is possible to use a hemocyte preparation in a single, routine assay to classify a microorganism present within a test sample. For example, the method permits one to determine whether microbes harvested or isolated from a sample of interest are a Gram negative bacteria, a Gram positive bacteria, or a fungi, for example, a yeast or mold.

The method comprises the steps of: (a) combining the sample of interest with a hemocyte preparation to produce a mixture; (b) measuring either (i) an optical property of the mixture at a preselected time or (ii) a time in which a preselected change occurs in an optical property of the mixture; and (c) comparing the optical property of step (b)(i) or the time value of step (b)(ii) with one or more (for example, two or three) standard values to determine whether a Gram negative bacterium, a Gram positive bacterium, or a fungus, for example, a yeast or a mold, is present in the sample.

In one assay format where the measurement step involves measuring an optical property of the mixture at a preselected time (i.e., step (b)(i)), it is understood from calibration assays that a first value of the optical property can be indicative of the presence of a Gram negative bacterium in the sample, a second value of the optical property can be indicative of the presence of a fungus in the sample, and a third value of the optical property can be indicative of the presence of a Gram positive bacterium in the sample. A variety of different optical properties can be used in the practice of the invention. The optical property can be, for example, the absorbance units or transmittance units of light at a preselected wavelength. Alternatively, the optical property measured can be the turbidity of the sample.

In another assay format where the measurement step involves measuring a time in which a preselected change occurs in an optical property of the mixture (i.e., step (b)(ii)), it is understood from calibration assays that a first time value can be indicative of the presence of a Gram negative bacterium in the sample, a second time value can be indicative of the presence of a fungus in the sample, and a third time value can be indicative of the presence of a Gram positive bacterium in the sample. The optical property can be, for example, the absorbance units or transmittance units of light of a preselected wavelength, or the turbidity of the sample.

The presence of each type of organism can be analyzed in separate individual assays or in a combined assay. For example, the assay may detect (i) Gram positive bacteria, (ii) Gram negative bacteria, (iii) fungus, (iv) a combination of Gram negative bacteria and Gram positive bacteria, (v) a combination of Gram negative bacteria and fungus, (vi) a combination of Gram positive bacteria and fungus, and (vii) a combination of Gram negative bacteria, Gram positive bacteria and fungus.

It is understood that a variety of hemocyte preparations can be useful in the practice of the invention. Hemocytes can be harvested from a variety of different organisms, for example, insects and crustaceans. Exemplary insects, include, silk worm larvae. Exemplary crustaceans include crabs belonging to the *Cancer* genus, for example, *Cancer borealis, Cancer irratus, Carcinus maenas, Hemigrapsus sanguineus* (Japanese Shore Crab), crabs belonging to the *Limulus* genus, for example, *Limulus polyphemus*, crabs belonging to the *Tachypleus* genus, for example, *Tachypleus gigas*, for example, *Tachypleus tridentatus*, and crabs belonging to the *Carcinoscorpius* genus, for example, *Carcinoscorpius rotundicauda*.

Hemocyte preparations useful in the practice of the invention can be derived from hemocytes by lysis using conventional techniques known in the art, for example, by osmotic shock, homogenization, ultrasonication and ultracentrifugation. For example, crude lysates may be produced using the procedure as originally described in Levin et al. (1968) THROMB. DIATH. HAEMORRH. 19: 186, with modification, or in Prior (1990) "Clinical Applications of the *Limulus* Amebocyte Lysate Test" CRC Press 28-36 and 159-166, and in U.S. Pat. No. 4,322,217.

In one embodiment, useful hemocyte preparations include a hemocyte lysate. Hemocyte lysates include any lysate or a fraction or component thereof, produced by the lysis and/or membrane permeabilization of hemocytes, for example, amebocytes and hemolymph cells, (i) extracted from a crustacean or insect and/or (ii) cultured in vitro after extraction from the host. Hemocyte cellular material that has been extruded from hemolymph cells by contact with a membrane permeabilization agent such as a $Ca^{2+}$ ionophore or the like (i.e., extruded other than by lysis) or otherwise extracted without cellular lysis is also considered to be a hemocyte lysate. A preferred hemocyte lysate is an amebocyte lysate prepared from the blood of a crustacean, for example, a horseshoe crab. It is also contemplated that hemocyte lysate may include a cocktail of one or more natural (e.g., purified) or synthetic components of the enzyme cascades shown in FIG. 1.

An amebocyte lysate is any lysate or fraction or component thereof produced by the lysis, extrusion, or extraction of the cellular contents from amebocytes extracted from a crustacean, for example, a horseshoe crab. The amebocyte lysate comprises at least one component of an enzymatic cascade (for example, as shown in FIG. 1) and/or produces a clot in the presence of an endotoxin, for example, a Gram negative bacterial endotoxin and/or a glucan, for example, a $(1\rightarrow3)$-$\beta$-D glucan, produced by a yeast or a mold. Preferred amebocyte lysates can be derived from horseshoe crabs, which include crabs belonging to the *Limulus* genus, for example, *Limulus polyphemus*, the *Tachypleus* genus, for example, *Tachypleus gigas*, and *Tachypleus tridentatus*, and the *Carcinoscorpius* genus, for example, *Carcinoscorpius rotundicauda*.

It is possible to produce an endotoxin-specific lysate by removing Factor G activity from the lysate, such as the Factor G depleted lysates produced by the methods described in U.S. Pat. Nos. 6,391,570 and 6,270,982. Also, it is contemplated that lysates may be depleted of Factor G activity by the addition of certain inhibitors or modulators of Factor G activity, for example, certain detergents, saccharides, polysaccharides, and other reagents described in U.S. Pat. Nos. 5,155,032; 5,179,006; 5,318,893; 5,474,984; 5,641,643; 6,270,982; and 6,341,570. An endotoxin-specific lysate is a lysate capable of reacting with a bacterial endotoxin but in which the reactivity to $(1\rightarrow3)$-$\beta$-D glucan has been depleted by at least 80%, more preferably by at least 90%, and more preferably by at least 95% relative to the crude lysate from which the endotoxin-specific lysate was prepared.

It is possible to produce a $(1\rightarrow3)$-$\beta$-D glucan specific lysate by producing a lysate depleted of Factor C activity. U.S. patent application, publication number US 2004/0241788, published Dec. 2, 2004 describes a method for producing a Factor G specific lysate. In this method, a glucan-specific lysate is prepared by lysing amebocytes in the presence of at least 0.15 M salt, more preferably 0.25 M salt, for example, a salt containing a monovalent cation, such as sodium or potassium ions. A glucan-specific lysate is a lysate capable of reacting with glycan, for example, $(1\rightarrow3)$-$\beta$-D glucan, but in which reactivity to a bacterial endotoxin or lipopolysaccharide has been depleted by at least 80%, more preferably at least 90%, and more preferably at least 95% relative to the crude lysate from which the glucan-specific lysate was prepared.

Furthermore, it is understood that useful hemocyte preparations may also include a combination of different lysates. For example, it is possible to produce a lysate useful in the practice of the invention by combining a lysate depleted of Factor G activity but retaining Factor C activity with a different lysate depleted of Factor C activity but retaining Factor G activity. The resulting lysate mixture contains both Factor C and Factor G activity.

As will be apparent to one of ordinary skill, divalent metal salts, which are known to promote activation of the pro-clotting enzyme of hemocyte lysate, as well as buffers to avoid extremes of pH that could inactivate the clotting enzyme preferably are included in the hemocyte preparations. Any of the buffers and salts that are understood in the art to be compatible with the amebocyte lysate system may be used. Typical formulation additives may include, without limitation, about 100-300 mM NaCl, about 10-100 mM divalent cations (e.g., $Mg^{2+}$ or $Ca^{2+}$), biocompatible buffers, e.g., Tris(tris(hydroxy)aminomethane), to give a final pH of about 6.0 to about 8.0, and, if the lysate is to be freeze dried, then sugars, e.g., mannitol or dextran. It is contemplated that the choice of appropriate formulation additives may also be determined by routine experimentation.

Synthetic chromogenic substrates have been used to measure the level of endotoxin-activated pro-clotting enzyme in LAL prepared from the hemolymph of both *Tachypleus tridentatus* and *Limulus polyphemus* horseshoe crabs (Iwanaga et al. (1978) HEMOSTASIS 7: 183-188). During an LAL assay that uses a chromogenic substrate, the pro-clotting enzyme (a serine protease) in the LAL is activated by endotoxin and cleaves the substrate's peptide chain on the carboxyl side of arginine so as to release the chromogenic group from the substrate, thereby releasing a marker compound that can be easily detected by, for example, spectrophotometry. One advantage of using a synthetic chromogenic substrate in an LAL assay in place of a conventional LAL gelation test is that the amount of activated clotting enzyme can be quantified and correlated to endotoxin levels in the sample.

Any chromogenic substrate that is cleaved by the clotting enzyme in a hemocyte preparation may be used in the practice of the invention. U.S. Pat. No. 5,310,657, for example, describes an exemplary chromogenic substrate having the formula $R_1$-$A_1$-$A_2$-$A_3$-$A_4$-B-$R_2$, where $R_1$ represents hydrogen, a blocking aromatic hydrocarbon or an acyl group; $A_1$ represents an L or D-amino acid selected from Ile, Val or Leu; $A_2$ represents Glu or Asp; $A_3$ represents Ala or Cys; $A_4$ represents Arg; B represents a linkage selected from an ester and an amide; and $R_2$ represents a chromogenic of fluorogenic group which is covalently attached to the C-carboxyl terminal of Arginine through the B linkage, the fluorogenic or chromogenic moiety being capable of being cleaved from the remainder of the chromogenic substrate to produce a chromogen or a fluorogen. An exemplary chromogenic substrate has the consensus sequence acetate-Ile-Glu-Ala-Arg-pNA (SEQ ID NO: 1), where pNA represents a para-nitroaniline group.

U.S. Pat. No. 4,188,264 describes a peptide substrate with a structure consisting of L-amino acids in the sequence $R_1$-Gly-Arg-$R_2$ where $R_1$ represents an N-blocked amino acid and $R_2$ is a group that can be released by enzymatic hydrolysis to yield a colored compound, $HR_2$. U.S. Pat. No. 4,510,241 discloses a chromogenic peptide substrate, which differs from the previous substrate in that the Gly moiety is replaced in the sequence by Ala or Cys. Alternatively, the chromogenic substrate may contain a fluorophore, for example, 7-amino-4-methyl coumarin, 7-amino-4-trifluoromethyl coumarin, and 4-methoxy-2-naphthalyamine.

Assay Considerations

It is understood that the method of the invention can be facilitated using a variety of endpoint or kinetic assays. Exemplary endpoint assays include an endpoint chromogenic assay or an endpoint turbidimetric assay. Exemplary kinetic assays include a kinetic turbidimetric assay, a one-step kinetic assay or a multi-step kinetic assay. Each of the assays is discussed in more detail below. Furthermore, it is understood that the assays may be modified to be performed in a particular assay format, for example, in a cartridge or in the well of a plate, for example, a 96 well plate.

(1) Kinetic Assays

Exemplary kinetic assays include multi-step kinetic assays, single-step kinetic assays, and kinetic turbidimetric assays.

(i) Multi-Step Kinetic Assay

Figure 2:
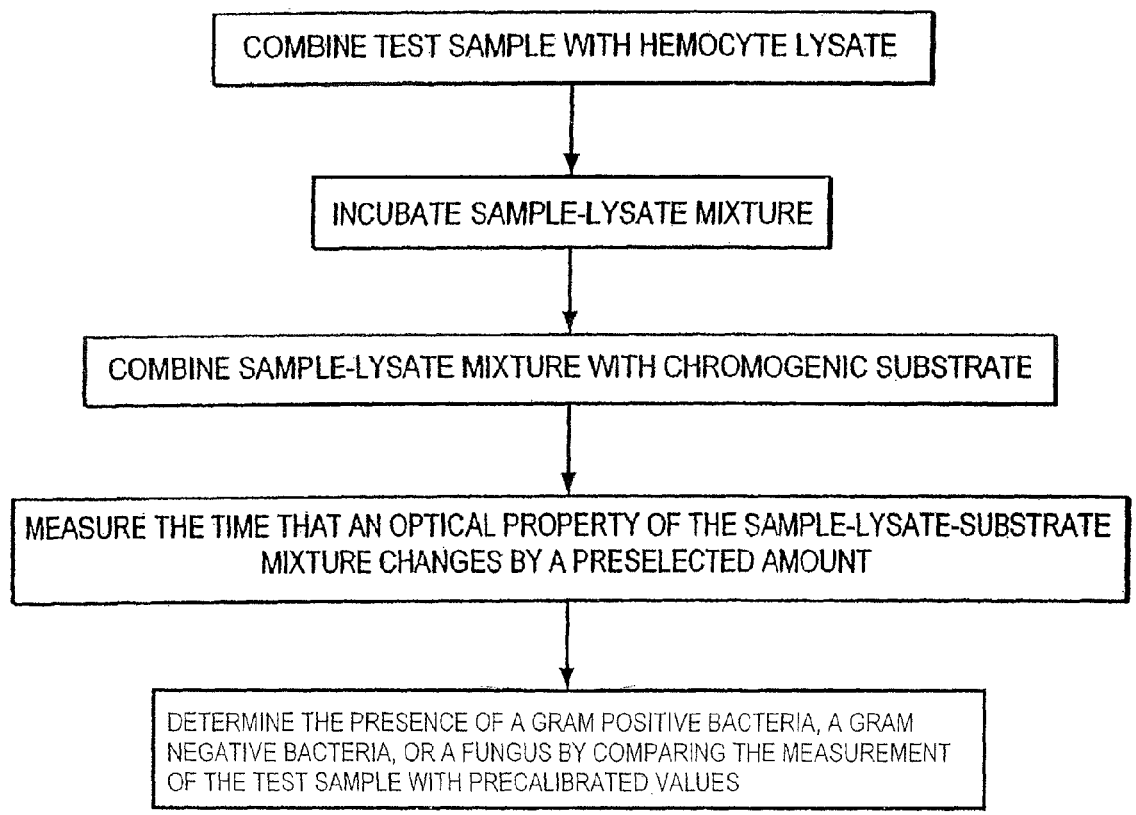
FIG. 2 is a flow chart showing an exemplary multi-step kinetic assay.

The various steps involved in the multi-step kinetic assay are shown schematically in FIG. 2. The assay is initiated by combining the sample to be tested with a volume of a hemocyte preparation to produce a sample-hemocyte preparation mixture. The mixture then is incubated for a predetermined period of time. The mixture then is contacted with a substrate, for example, a chromogenic substrate, to produce a sample-hemocyte preparation-substrate mixture. Thereafter, the time in which a preselected change in an optical property (for example, a specific change in an absorbance value or a specific change in a transmission value) is measured.

The assay can be calibrated by measuring the time in which a preselected change in an optical property occurs when a certain amount of a Gram negative bacteria, a Gram positive bacteria or a fungus are introduced into the assay. It is understood that Gram negative bacteria give a first value, for example, a first range of time points, fungi give a second value, for example, a second range of time points, and Gram positive bacteria give a third value, for example, a third range of time points. The first, second and third values preferably do not overlap with one another. By comparing the result generated by a test sample against one or more of the first, second and third values, it is possible to determine whether the microbe present in the test sample is a Gram negative bacteria, a Gram positive bacteria, or a fungi.

It is understood that a multi-step kinetic assay can be run in a cartridge format. The cartridge preferably is used with an optical detector, for example, a hand-held optical detector as shown and described in U.S. Pat. No. Des. 390,661.

By way of example and as illustrated in FIGS. 3A-3D, cartridge 1 has a substantially planar housing fabricated, for example, from a moldable biocompatible material. The housing may be fabricated from any material, however, transparent and/or translucent glass or polymers are preferred. Preferred polymers include, for example, polystyrene, polycarbonate, acrylic, polyester, optical grade polymers, or any plastic such that the optical cell is substantially transparent. The housing contains at least one fluid inlet port 4, at least one optical cell 6, and at least one conduit 8 having a fluid contacting surface for providing fluid flow communication between the fluid inlet port 4 and optical cell 6. The only requirements for the optical cell 6 are that it defines a void capable of containing a sample to be tested and that a portion of the optical cell 6 is transparent to light. Cartridge 1 may also have at least one pump port 12 in fluid flow communication with fluid inlet port 4 and optical cell 6 for attaching the cartridge 1 to a pump. The pump may then impart a negative pressure via pump port 12 to pull the sample from fluid inlet port 4 to optical cell 6. A hemocyte lysate is disposed on a first region 14 of the fluid contacting surface of conduit 8, so that when a sample is applied to fluid inlet port 4, the sample traverses region 14 and solubilizes or reconstitutes the hemocyte lysate into the sample as it moves toward optical cell 6.

A second region 16 of the fluid contacting surface of conduit 8 is spaced apart from and downstream of first region 14. In this configuration, hemocyte lysate is disposed at first region 14 and a chromogenic substrate is disposed at second region 16, so that after the sample is contacted with the hemocyte lysate in region 14, the sample-lysate mixture traverses conduit 8 and contacts the chromogenic substrate in region 16. The sample-lysate-substrate mixture then traverses conduit 8 to optical cell 6.

The cartridges can be designed and used according to the type and/or number of tests required. For example, a single sample may be tested, for example, in duplicate or triplicate, for example, for research laboratory use or for medical device and biopharmaceutical testing. Alternatively, two or more different samples may be tested individually, for example, for dialysis facility testing of water and dialysate. The cartridge preferably is a single-use, disposable cartridge that is discarded after one use. The cartridges typically use approximately 20-100 fold less hemocyte lysate per sample than is used in the conventional endpoint chromogenic or kinetic chromogenic assays performed in multi-well plates, and thus provides a less costly and environmentally-friendlier test.

Figure 3A:
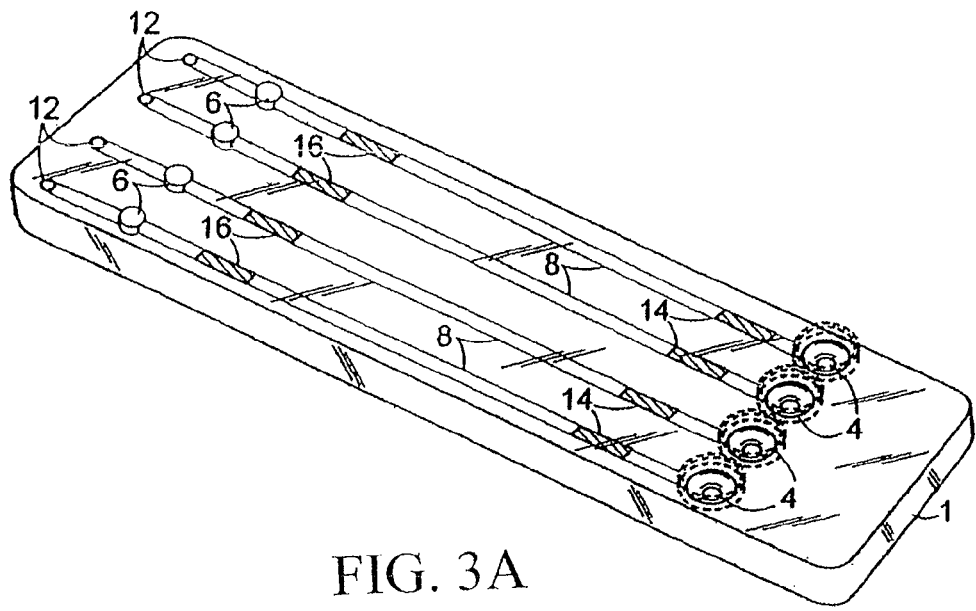
FIGS. 3A-3D are schematic illustrations of an exemplary cartridge in perspective view (FIG. 3A), top view (FIG. 3B), side view (FIG. 3C), and end view (FIG. 3D)
Figure 3B:
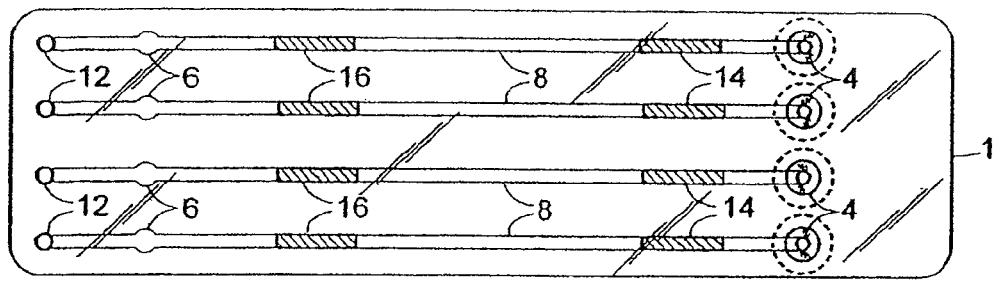
Figure 3C:
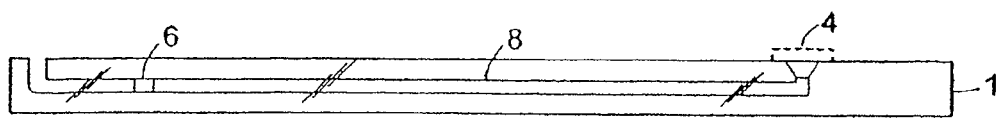
Figure 3D:
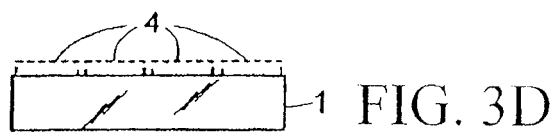

With reference to FIG. 3A, in order to perform a multi-step kinetic assay in an exemplary cartridge 1, a sample is first moved, for example, by pump action, to a first region 14 containing the hemocyte preparation, where it is mixed and incubated for a predetermined period of time. The sample-hemocyte preparation mixture then is moved, for example, by pump action, to the second region 16 containing the substrate, for example, a chromogenic substrate, where it is solubilized. The sample-chromogenic substrate mixture then is moved to optical cell 6, for a measurement of an optical property. The time intervals required for mixing and incubating steps are preprogrammed for optimal sensitivity and microbial contaminant concentration range. An exemplary cartridge-based multi-step kinetic assay is described in Example 1.

Although the multi-step assay may be performed in a cartridge of the type discussed above, it may also be employed in a variety of other formats, for example, within the well of a microtiter plate. In this type of assay, a sample of interest is combined with a hemocyte preparation and incubated for a predetermined period of time. Then, after the predetermined period of time, a chromogenic substrate is added to the well. After mixing, the time in which a preselected change in an optical property occurs is measured. The result can then be compared against one or more standard values to determine whether Gram negative bacteria, Gram positive bacteria or fungus is present in the sample of interest.

In the well-type format, the samples and reagents are added to each of the wells, preferably using an automated system, such as a robot, and the plate processed by a microplate reader, which can be programmed to sequentially read the absorbance of each well in a repetitive fashion.

(ii) Single-Step Kinetic Assay

A single-step kinetic assay, for example, a single step-chromogenic assay, is described in U.S. Pat. No. 5,310,657. Briefly, the kinetic chromogenic assay includes the steps of (i) simultaneously solubilizing a hemocyte preparation with a sample to be analyzed and a substrate, for example, a chromogenic substrate, (ii) incubating the resulting mixture at a temperature of about 0° to about 40° C., preferably about 25° to about 40° C., over a predetermined time range, and (iii) measuring a time required for a colorimetric change to reach a pre-selected value or change of the colorimetric readout, using a conventional spectrophotometer.

This type of assay, like the multi-step kinetic assay, can be performed in a cartridge or a well-type format. A cartridge similar to that described above for the multi-step kinetic assay can be modified for use in single-step kinetic assay. With reference to FIG. 3A, chromogenic substrate is applied, for example, to the surface of conduit 8 at first region 14 together with the hemocyte lysate. In order to perform a kinetic chromogenic assay in cartridge 1 and in reference to FIG. 3A, a sample is moved, for example, by pump action, to a first region 14 of the conduit 8 containing both the hemocyte preparation and chromogenic substrate, where they are solubilized, for example, by cycling between forward and reverse pump action. The sample-hemocyte preparation-substrate mixture then is moved to optical cell 6 for measurement of an optical property, for example, the absorbance or transmittance properties of the sample by an optical detector. The detector may determine how long it takes for each optical property to exhibit, for example, a 5% drop in optical transmittance. Results from multiple assays, for example, two assays, can be averaged.

The assay can be calibrated by measuring the time in which a preselected change in an optical property occurs when a certain amount of Gram negative bacteria, Gram positive bacteria or fungi are introduced into the assay. It is understood that Gram negative bacteria give a first value, for example, a first range of time points, fungi give a second value, for example, a second range of time points, and Gram positive bacteria give a third value, for example, a third range of time points. The first, second and third values preferably do not overlap with one another. By comparing the result generated by a test sample against one or more of the first, second and third values, it is possible to determine whether the microbe present in the test sample includes a Gram negative bacteria, a Gram positive bacteria or a fungi.

This type of assay format may be employed in a variety of other formats, for example, within the well of a microtiter plate. In this type of assay, a sample of interest is mixed with a hemocyte preparation and a chromogenic substrate. After mixing, the time in which a preselected change in an optical property occurs is measured. The result can then be compared against standard values to determine whether Gram negative bacteria, Gram positive bacteria, or fungus is present in the sample of interest. An exemplary well-based single-step kinetic assay is described in Example 3.

(iii) Kinetic Turbidimetric Assay

The kinetic turbidimetric assay is described in Prior (1990) supra, pp. 28-34. Briefly, the kinetic turbidimetric assay includes the steps of (i) solubilizing a hemocyte lysate with a sample to be analyzed, (ii) incubating the resulting mixture at a temperature of about 0° to about 40° C., preferably about 25° to about 40° C., over a predetermined time range, and (iii) measuring a time required for either a turbidity change caused by coagulation to reach a pre-selected value or a ratio in change of the turbidity, using a conventional coagulometer, nepherometer, or spectrophotometer.

This type of assay, like the previous assays, can be performed in a cartridge or a well-type format. A cartridge similar to that described above for the multi-step or single-step kinetic assays can be modified for use in kinetic turbidimetric assays. With reference to FIG. 3A, no chromogenic substrate needs to be applied to either first region 14 or second region 16.

Referring to FIG. 3A, in order to perform a kinetic turbidimetric assay in a cartridge 1, a sample is, for example, moved to a first region 14 of the conduit 8 containing the hemocyte preparation, where it is solubilized, for example, by cycling between forward and reverse pump action. The sample-lysate mixture then is moved to optical cell 6 for measurement of an optical property, for example, turbidity, by measuring, for example, the absorbance or transmittance properties of the sample-lysate mixture using an optical detector. The detector may determine how long it takes for each optical property to exhibit, for example, a 5% drop in optical transmittance. Results from multiple assays, for example, two assays can be averaged.

The assay can be calibrated by measuring the time in which a preselected change in an optical property, for example, turbidity, occurs when a certain amount of a Gram negative bacteria, Gram positive bacteria or a fungi are introduced into the assay. It is understood that Gram negative bacteria give a first value, for example, a first range of time points, fungi give a second value, for example, a second range of time points, and Gram positive bacteria give a third value, for example, a third range of time points. The first, second and third values preferably do not overlap with one another. By comparing the result generated by a test sample against the first, second and third values, it is possible to determine whether the microbe present in the test sample includes Gram negative bacteria, Gram positive bacteria or fungi.

This type of assay format may be employed in a variety of other formats, for example, within the well of a microtiter plate. In this type of assay, a sample of interest is mixed with a hemocyte preparation. After mixing, the time in which a preselected change in an optical property, for example, turbidity, occurs is measured. The result can then be compared against standard values to determine whether Gram negative bacteria, Gram positive bacteria, or fungus is present in the sample of interest. An exemplary well-based kinetic turbidimetric assay is described in Example 2.

(2) Endpoint Assays

Exemplary endpoint assays include endpoint chromogenic and endpoint turbidimetric assays.

(i) Endpoint Chromogenic Assay

The endpoint chromogenic assay is described in Prior (1990) supra, pp. 28-34, and U.S. Pat. Nos. 4,301,245 and 4,717,658. Briefly, the endpoint chromogenic assay includes the steps of (i) solubilizing a hemocyte preparation with a sample to be analyzed, (ii) incubating the resulting mixture at a temperature of about 0° C. to about 40° C., preferably about 25° C. to about 40° C., for a predetermined time, (iii) contacting substrate, for example, a chromogenic substrate, with the incubated sample-hemocyte preparation mixture, (iv) optionally adding a reaction inhibitor, for example, acetic acid, and (v) measuring, e.g., by colorimetric change, a substance produced from the substrate by enzymatic activity.

This type of assay can be performed in a cartridge or in a well-type format. When an endpoint chromogenic assay is performed in a cartridge 1 (see, FIG. 3A), a sample is moved, for example, to a first region 14 of the conduit 8 containing the hemocyte preparation, where it is solubilized, for example, by cycling between forward and reverse pump action. Following a predetermined incubation period, the sample-hemocyte preparation mixture then is moved, for example, by pump action to a second region 16 of the conduit 8 containing the chromogenic substrate, where it is solubilized, for example, by cycling between forward and reverse pump action. The sample-hemocyte preparation-substrate mixture optionally then is moved to a third region containing a reaction inhibitor. Afterwards, the sample-hemocyte preparation-substrate mixture is moved to optical cell 6 for measurement of an optical property, for example, the absorbance or transmittance properties of the sample by an optical detector. It is contemplated, however, that when performing an end-point chromogenic assay in a cartridge it is not necessary to stop the reaction using a reaction inhibitor. Under this type of assay, the final optical readings (endpoint readings) are recorded at a predetermined time.

The assay can be calibrated by measuring an optical property, for example, absorbance or transmittance, when a certain amount of Gram negative bacteria, Gram positive bacteria or fungi are introduced into the assay. It is understood that Gram negative bacteria give a first value, for example, a first range of absorbance or transmittance values, fungi give a second value, for example, a second range of absorbance or transmittance values, and Gram positive bacteria give a third value, for example, a third range of absorbance or transmittance values. The first, second and third values preferably do not overlap with one another. By comparing the result generated by a test sample against one or more of the first, second and third values, it is possible to determine whether the microbe present in the test sample includes Gram negative bacteria, Gram positive bacteria or fungus.

As discussed, this type of assay format may be employed in a variety of other formats, for example, within the well of a microtiter plate. In this type of assay, a sample of interest is mixed with a hemocyte preparation and incubated for a preselected period of time. Then, a chromogenic substrate is added to the mixture and the sample incubated for another period of time. Then a reaction inhibitor, for example, acetic acid, is added to the sample, and an optical property of the sample, for example, absorbance or transmittance is measured. The result can then be compared against standard values to determine whether Gram negative bacteria, Gram positive bacteria, or fungi are present are the sample of interest. An exemplary well-based endpoint chromogenic assay is described in Example 4.

(ii) Endpoint Turbidimetric Assay

The endpoint turbidimetric assay is described in Prior (1990) supra, pp. 28-34. Briefly, the end point turbidimetric assay includes the steps of (i) solubilizing a hemocyte lysate with a sample to be analyzed, (ii) incubating the resulting mixture at a temperature of about 0° to about 40° C., preferably about 25° to about 40° C., for a predetermined time, (iii) optionally adding a reaction inhibitor, for example, acetic acid, and (iv) measuring the increase in turbidity as a result of coagulation, if any, using a conventional coagulometer, nephrometer, or spectrophotometer.

Endpoint turbidimetric assays can be performed in a cartridge-type format. With reference to FIG. 3A, a sample is applied to cartridge 1 and is moved, for example, to a first region 14 of the conduit 8 containing the hemocyte lysate, where it is solubilized, for example, by cycling between forward and reverse pump action. The sample-lysate mixture then is moved to optical cell 6 for measurement of an optical property, for example, turbidity, using an optical detector. Results from multiple assays, for example, two assays can be averaged.

The assay can be calibrated, for example, by measuring the turbidity at a preselected time when a certain amount of Gram negative bacteria, Gram positive bacteria or fungi are introduced into the assay. It is understood that Gram negative bacteria give a first value, for example, a first range of turbidity values, fungi give a second value, for example, a second range of turbidity values, and Gram positive bacteria give a third value, for example, a third range of turbidity values. The first, second and third values preferably do not overlap with one another. By comparing the result generated by a test sample against one or more of the first, second and third values, it is possible to determine whether the microbe present in the test sample includes a Gram negative bacterium, a Gram positive bacterium or a fungus.

This type of assay format may also be run in other formats, for example, within the well of a microtiter plate. In this type of assay, a sample of interest is mixed with a hemocyte preparation and incubated for a preselected period of time. The reaction can then be stopped by the addition of an inhibitor. An optical property, for example, turbidity, of the sample then is measured at a preselected time point. The result can then be compared against standard values to determine whether Gram negative bacteria, Gram positive bacteria, or fungus is present in the sample of interest.

Specimen Collection and Preparation Considerations

In general, materials used to harvest, store, or otherwise contact a sample to be tested, as well as test reagents, should be free of microbial contamination, for example, should be pyrogen-free. Materials may be rendered pyrogen-free by, for example, heating at 250° C. for 30 minutes. Appropriate precautions should be taken to protect depyrogenated materials from subsequent environmental contamination.

Once the sample has been harvested, the microbial contaminants preferably are cultured under aseptic conditions to provide individual colonies. The use of an 18-24 hour isolated culture may provide optimal results. The colonies then are carefully removed from the culture plates to avoid contaminating the culture with fragments of the growth media. The cells then are suspended in a lipopolysaccharide-free solution, for example, saline or water. The resulting suspensions can then be assayed using one or more of the assays described herein.

The assays may be used to classify the type of microbe present in a sample of interest, for example, in a fluid, for example, a fluid to be administered locally or systemically, for example, parenterally to a mammal, or a body fluid to be tested for infection, including, for example, blood, lymph, urine, serum, plasma, ascites fluid, lung aspirants, and the like. In addition, the assays may be used to classify the type of microbe present in a water supply, for example, a supply of drinking water. In addition, the assays of the invention may be used to classify the type of microbial contaminant present in a food product, pharmaceutical, or medical device. Furthermore, the assays of the invention can be used to classify the type of microbe present on a surface. For example, the surface of interest is swabbed and the swab then is introduced into or dissolved in liquid. The liquid can then be assayed as described herein.

EXAMPLES

Practice of the invention will be more fully understood from the following examples, which are presented herein for illustrative purposes only, and should not be construed as limiting the invention in any way.

Example 1

Cartridge-based Multi-step Kinetic Assay

Figure 4A:
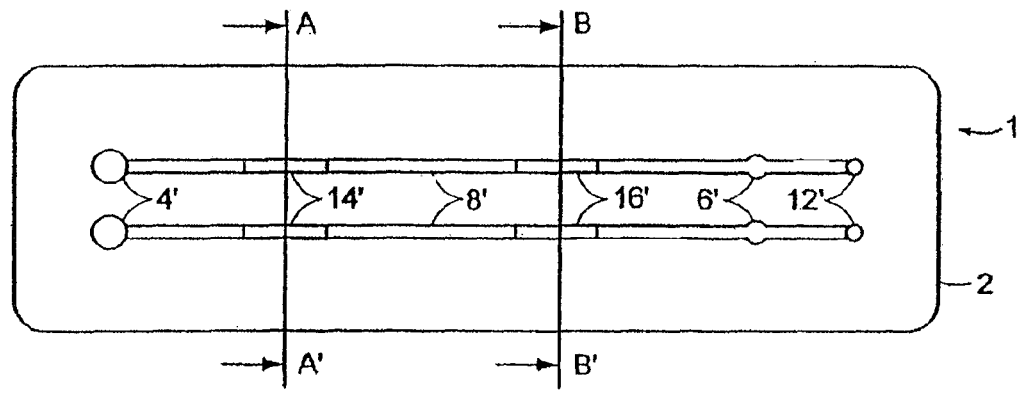
Figure 4B:
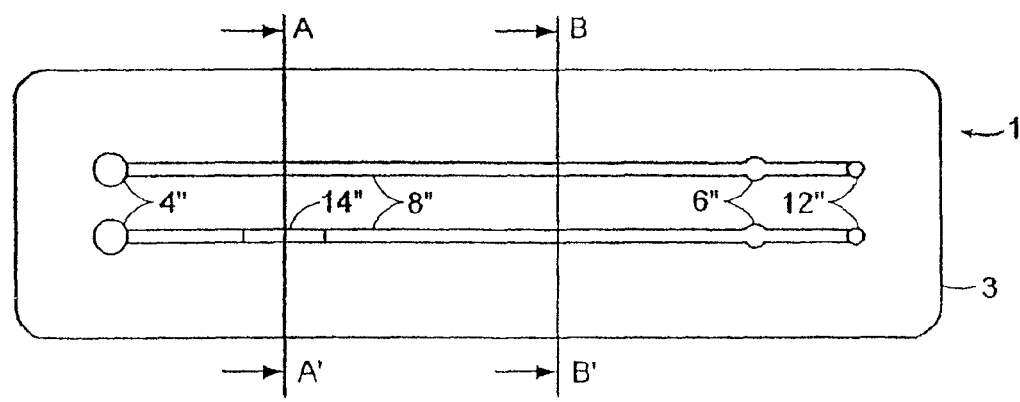
Figure 4C:
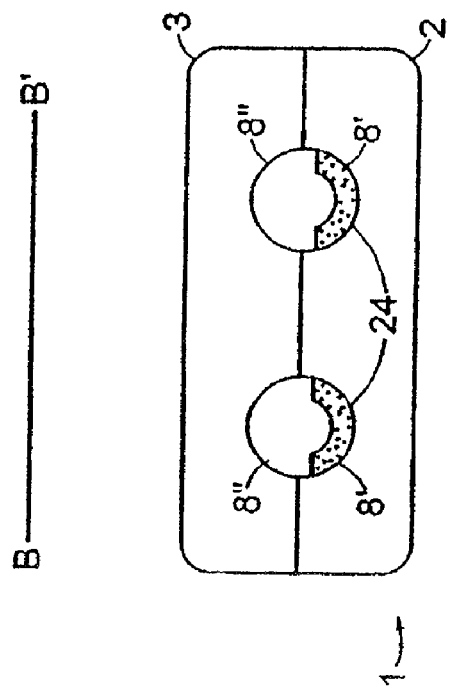
Figure 4D:
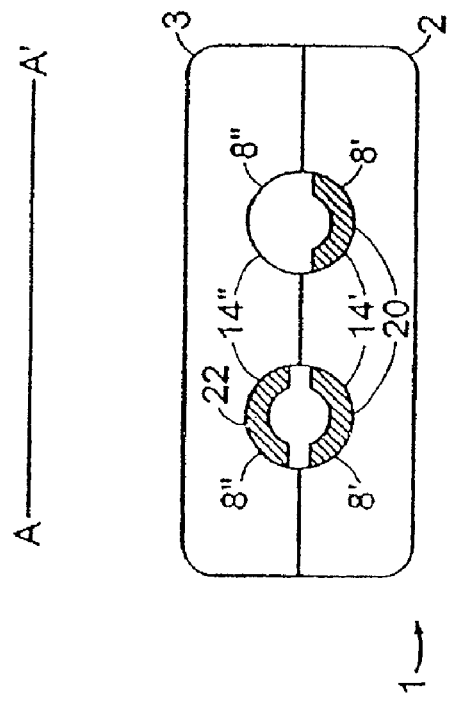

An exemplary cartridge shown in FIG. 3 was prepared as follows. Referring to FIG. 4A, the LAL and chromogenic substrates were applied to regions 14' and 16', respectively, of conduit 8' of the bottom half 2 of the cartridge 1 using a Champion 3700 automated cartridge filler (Creative Automation Company, Sun Valley Calif.). Briefly, 4-5.0 µL of Endosafe LAL (Charles River Endosafe, Charleston, S.C.) containing 1% mannitol (Osmitrol, Baxter, Deerfield, Ill.) and 0.1% dextran (MW 10-100K, Sigma-Aldrich, St. Louis, Mo.), was applied to regions 14'. 4-5.0 µL of (1.3 mg/mL) chromogenic substrate Ile-Glu-Ala-Arg-pNA Chromogenix S-2423 (Instrumentation Laboratories, Milan, Italy) containing 1% polyvinyl alcohol (PVA) (MW 7K-30K, Sigma-Aldrich, St. Louis, Mo.), was applied to regions 16'. The bottom half 2 of the cartridge 1 was dried under a controlled temperature of 25° C.+/−2° C. and a humidity of 5%+/−5% in a Lunaire Environmental Steady State & Stability Test Chamber (Lunaire Environmental, Williamsport, Pa.) in a Puregas HF200 Heatless Dryer (MTI Puregas, Denver, Colo.) for 1 hour. Temperature and humidity was controlled by a Watlow Series 96 1/16 DIN Temperature Controller (Watlow Electric Manufacturing Company, St. Louis, Mo.).

Following fabrication, the two halves 2 and 3 were assembled such that regions 14' and 14" were aligned one on top of the other, and the edges of the cartridge halves 2 and 3 ultrasonically sealed using a Dukane Model 210 Ultrasonic Sealer (Dukane Corporation, St. Charles, Ill.) under the control of a Dukane Dynamic Process Controller (Dukane Corporation, St. Charles, Ill.).

Multi-step kinetic assays then were performed using the cartridges as described in more detail hereinbelow. Briefly, several species of microorganisms listed in Table 1 were obtained from the America Type Culture Collection (ATCC) and grown on standard microbiological growth medium containing agar in Petri dishes under standard conditions. After overnight growth, individual colonies were removed from the surface of the agar using a sterile loop. The colonies then were suspended in sterile, clean saline (free of LPS or other bacterial contamination). The density of the suspension was adjusted to give a density of 0.5 units on the McFarland equivalence turbidity standard.

A cartridge then was inserted into an Endosafe Portable Test System (PTS) obtained from Charles River Endosafe, Charleston, S.C. Then, 25 µL of each suspension was placed in an individual sample well of a cartridge. The sample was drawn into the cartridge by the PTS. Initially, the sample was combined with the hemocyte preparation. After a defined period of time, the sample was mixed with the chromogenic substrate (p-nitro aniline). The degree of reactivity in each sample was measured by kinetic reading of color development at 395 nm. The results are summarized in Table 1 and represent the time (in seconds) that elapsed to reach a particular color density (onset O.D.).

TABLE 1

| Microorganism Tested | Type | Time to reach Onset O.D. (seconds) |
|---|---|---|
| *Pseudomonas aeruginosa* (ATCC 27853) | Gram negative | 18 |
| *Escherichia coli* (ATCC 8739) | Gram negative | 20 |
| *Staphylcoccus aureus* (ATCC 6538) | Gram positive | 1200 |
| *Bacillus subtilis* (ATCC 6633) | Gram positive | 1200 |
| *Candida albicans* (ATCC 10231) | Yeast | 271 |
| *Aspergillus niger* (ATCC 16404) | Mold | 250 |

The results summarized in Table 1 demonstrate that, under the conditions tested, the Gram-negative bacteria took 18-20 seconds to reach the onset O.D., yeast and mold took 250-271 seconds to reach the onset O.D., and Gram positive bacteria took 1200 seconds to reach the onset O.D. As a result of various studies, it has been found that the onset times for Gram-negative bacteria routinely can be less than 150 seconds, the onset times for yeast and molds routinely can range from 151 to 399 seconds, and the onset times for Gram-positive bacteria routinely can take 400 seconds or greater. Based on the onset times generated by a test sample, this assay can be used to determine whether Gram negative bacteria, fungi, or Gram positive bacteria are present in a sample of interest.

Example 2

Well-Based Kinetic Turbidimetric Assay

A large number of samples may be run in a multi-welled microplate using Kinetic Turbidimetric Assay techniques. KTA reagent LAL Lot U2251L (R1900 KTA[2], Charles River Endosafe, Charleston, S.C.) was prepared according to manufacturers directions and mixed with an equal volume of microbial suspension (0.5 McFarland Units). The reaction was performed in accordance with the manufacturers instructions. The time to reach onset O.D. (in seconds) was recorded for individual suspensions of *E. coli*, (gram negative), *S. aureus* (gram positive), and *C. albicans* (a yeast). Samples were run in triplicate. The results are summarized in Table 2.

TABLE 2

| Microorganism Tested | Type | Time to reach Onset O.D. (seconds) |
|---|---|---|
| *Escherichia coli* (ATCC 8739) | Gram negative | 384.2 |
| | | 388.7 |
| | | 386.4 |
| *Candida albicans* (ATCC 10231) | Yeast | 1464.4 |
| | | 1509.4 |
| | | 1489.3 |
| *Staphylococcus aureus* (ATCC 6633) | Gram positive | >3600.0 |
| | | >3600.0 |
| | | >3600.0 |

Although the standard kinetic turbidimetric method was slower than the multi-step kinetic chromogenic method used in Example 1, the overall results were the same. Gram type was interpreted by the degree of reactivity with LAL. The results indicate that, under the conditions tested, the Gram-negative bacteria took 384-388 seconds to reach the onset O.D., yeast took 1464-1509 seconds to reach the onset O.D., and Gram positive bacteria took more than 3600 seconds to reach the onset O.D. This assay can be used to classify a microorganism in a test sample. For example, this assay, based on the onset times generated by a test sample, can be used to determine whether Gram negative bacteria, fungi, or Gram positive bacteria is present in a sample of interest.

Example 3

Well-Based Kinetic Chromogenic Assay

Large numbers of samples can be run using the Kinetic Chromogenic LAL assay in a multi-well microplate. LAL Lot U4132E (R170Endochrome-k, Charles River Endosafe, Charleston, S.C.) was prepared according to manufacturers directions and mixed with an equal volume of microbial suspension (0.5 McFarland Units). The reaction was performed in accordance with the manufacturers instructions. The time to reach onset O.D. (in seconds) was recorded for individual suspensions of *E. coli*, (gram negative), *S. aureus* (gram positive) and *C. albicans* (a yeast). Samples were run in triplicate. The results are summarized in Table 3.

TABLE 3

| Microorganism Tested | Type | Time to reach Onset O.D. (seconds) |
|---|---|---|
| *Escherichia coli* (ATCC 8739) | Gram negative | 213.0 218.4 215.1 |
| *Candida albicans* (ATCC 10231) | Yeast | 882.4 889.7 874.2 |
| *Staphylococcus aureus* (ATCC 6633) | Gram positive | 3061.9 3032.5 2463.5 |

Although the standard kinetic chromogenic assay was slower than the multi-step kinetic chromogenic method used in Example 1, the overall results were the same. Gram type was interpreted by the degree of reactivity with LAL. The results indicate that, under the conditions tested, the Gram-negative bacteria took 213-218 seconds to reach the onset O.D., yeast took 874-889 seconds to reach the onset O.D., and Gram positive bacteria took 2463-3061 seconds to reach the onset O.D. Accordingly, this assay can be used to classify a microorganism in a test sample. For example, this assay, based on the onset times generated by a test sample, can be used to determine whether Gram negative bacteria, fungi, or Gram positive bacteria is present in a sample of interest.

Example 4

Well-Based Endpoint Chromogenic Assay

Samples were run using the Endpoint Chromogenic LAL assay in a multi-well microplate. LAL Lot T2092CT (R160Endochrome, Charles River Endosafe, Charleston, S.C.) was prepared according to manufacturers directions and mixed with an equal volume of microbial suspension (0.5 McFarland equivalence turbidity standard). The reaction was performed in accordance with the manufacturers instructions. At the conclusion of the test, reactions were stopped by adding an equal volume of 20% acetic acid and the optical density at 405 nm was recorded for individual suspensions of *E. coli* (Gram negative), *S. aureus* (Gram positive) and *C. albicans* (yeast). Samples were run in triplicate. The degree of reactivity in this case, was measured in final optical density for each sample. The results are summarized in Table 4.

TABLE 4

| Microorganism Tested | Type | Optical Density |
|---|---|---|
| *Escherichia coli* (ATCC 8739) | Gram negative | 1.9770 2.3670 2.4380 |
| *Candida albicans* (ATCC 10231) | Yeast | 0.1930 0.1840 0.1930 |
| *Staphylococcus aureus* (ATCC 6633) | Gram positive | 0.0200 0.0220 0.0250 |

Under the conditions tested, Gram negative bacteria had much greater reactivity due to its LPS content and resulted in O.D. readings of 1.97-2.43. The yeast had less reactivity (0.18-0.19) and Gram positive bacteria had very low reactivity (~0.02). Gram type was interpreted by the degree of reactivity with LAL. Accordingly, this assay can be used to classify a microorganism in a test sample. For example, this assay, based on the O.D. values generated by a test sample, can be used to determine whether Gram negative bacteria, fungi, or Gram positive bacteria were present in the sample of interest.

Example 5

Further Testing of Cartridge-Based Multi-Step Kinetic Assay

Cartridges were prepared and used essentially as described in Example 1. In this example, the microbial isolates tested and properly identified are listed in Table 5.

TABLE 5

| Microorganism Name | Gram Type |
|---|---|
| *Acinetobacter baumannii* | Gram-negative |
| *Acidovorax delafieldii* | Gram-negative |
| *Aeromonas veronii* | Gram-negative |
| *Alicyclobacillus acidocaldarius* | Gram-positive |
| *Aquaspirrilium sp.* | Gram-negative |
| *Aspergillus niger* | Mold |
| *Bacillus cereus* | Gram-positive |
| *Bacillus circulans* | Gram-positive |
| *Bacillus dipsosauri* | Gram-positive |
| *Bacillus licheniformis* | Gram-positive |
| *Bacillus pumilus* | Gram-positive |
| *Bacillus sphaericus* | Gram-positive |
| *Bacillus subtilis* | Gram-positive |
| *Bacillus thuringensis* | Gram-positive |
| *Bordetella bronchiseptica* | Gram-negative |
| *Brevibacillus choshinensis* | Gram-positive |
| *Brevibacterium brevis* | Gram-positive |
| *Burkholderia cepacia* | Gram-negative |
| *Candida albicans* | Yeast |
| *Candida guillermondii* | Yeast |
| *Candida parapilosis* | Yeast |
| *Comamonas (Delftia) acidovorans* | Gram-negative |
| *Citrobacter braaki* | Gram-negative |
| *Citrobacter freundii* | Gram-negative |
| *Clostridum sporogenes* | Gram-positive |

TABLE 5-continued

| Microorganism Name | Gram Type |
| --- | --- |
| Corynebacterium renale | Gram-positive |
| Cryptococcus humicolus | Yeast |
| Cryptococcus neoformans | Yeast |
| Cryseobacterium gleum | Gram-negative |
| Deinococcus radiodurans | Gram-positive |
| Enterobacter cloacae | Gram-negative |
| Enterobacter intermedius | Gram-negative |
| Enterococcus faecalis | Gram-positive |
| Escherichia coli | Gram-negative |
| Flavobacterium odoratum | Gram-negative |
| Geobacillus sterothermophilus | Gram-positive |
| Hydrogenophaga palleronii | Gram-negative |
| Klebsiella oxytoca | Gram-negative |
| Klebsiella pneumoniae | Gram-negative |
| Kocuria kristinae | Gram-positive |
| Kocuria rhizophila | Gram-positive |
| Kocuria rosea | Gram-positive |
| Listeria monocytogenes | Gram-positive |
| Microbacterium saperdaem | Gram-positive |
| Micrococcus species | Gram-positive |
| Morganella morganii | Gram-negative |
| Neisseria meningitidis serogroup B | Gram-negative |
| Ochrobactrum anthropi | Gram-negative |
| Paenibacillus glucanolyticus | Gram-positive |
| Paenibacillus polymyxa | Gram-positive |
| Pantoea ananas | Gram-negative |
| Paracoccus marcusii | Gram-negative |
| Propionibacterium acnes | Gram-positive |
| Pseudomonas aeruginosa | Gram-negative |
| Pseudomonas fluorescens | Gram-negative |
| Pseudomonas putida | Gram-negative |
| Pseudomonas stutzeri | Gram-negative |
| Proteus vulgaris | Gram-negative |
| Providencia rettgeri | Gram-negative |
| Ralstonia eutropha | Gram-negative |
| Ralstonia picketti | Gram-negative |
| Rhodococcus equi | Gram-positive |
| Rhodotorula glutinus | Yeast |
| Rhodotorula rubra | Yeast |
| Salmonella typhimurium | Gram-negative |
| Serratia liquefaciens | Gram-negative |
| Serratia marcescens | Gram-negative |
| Staphylococcus aureus | Gram-positive |
| Staphylococcus auricularis | Gram-positive |
| Staphylococcus capitis | Gram-positive |
| Staphylococcus epidermidis | Gram-positive |
| Staphylococcus pasteuri | Gram-positive |
| Staphylococcus warneri | Gram-positive |
| Stenotrophomonas maltophila | Gram-negative |
| Streptococccus pyogenes | Gram-positive |
| Streptococcus sanguis | Gram-positive |
| Yersinia kristensenii | Gram-negative |

During the experiments, it was observed that *Bacillus cereus*, a gram positive organism known to produce extracellular proteases in aged cultures gave spurious results in cultures grown for more than 24 hours. Repeated testing of cultures up to 24 hours gave the proper Gram identification. Furthermore, it was found that *Sphingomonas paucimobilis* did not produce the expected result. Without wishing to be bound by theory, it is contemplated that this organism, which is a rare Gram negative bacterial species lacking lipopolysaccharide, did not react with the LAL under the conditions used for this experiment.

Notwithstanding, the results summarized in this Example demonstrate that this method has general applicability for identifying whether Gram positive bacteria, Gram negative bacteria or fungus are present in a sample of interest.

Equivalents

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

INCORPORATION BY REFERENCE

All publications and patent documents cited in this application are incorporated by reference in their entirety for all purposes to the same extent as if the entire contents of each individual publication or patent document was incorporated herein.

What is claimed is:

1. A method of classifying a bacterium in a test sample, the method comprising the steps of:
    (a) combining the test sample, which contains a standardized amount of the bacterium, with a hemocyte preparation to produce a mixture;
    (b) measuring either (i) an optical property of the mixture at a preselected time or (ii) a time in which a preselected change occurs in an optical property of the mixture, wherein the optical property is selected from the group consisting of absorbance, transmittance, optical density, and turbidity; and
    (c) comparing the optical property of step (b)(i) or the time value of step (b)(ii) with a first standard value indicative of the presence of Gram negative bacteria and a second standard value indicative of the presence of Gram positive bacteria thereby to determine whether the bacterium is a Gram negative bacterium or a Gram positive bacterium.

2. The method of claim 1, wherein in step (c), a first optical property is indicative of the presence of Gram negative bacteria in the sample and a second optical property is indicative of the presence of Gram positive bacteria in the sample.

3. The method of claim 1, wherein in step (c), a first time value is indicative of the presence of Gram negative bacteria in the sample, and a second time value is indicative of the presence of Gram positive bacteria in the sample.

4. The method of claim 1, wherein in step (b)(i), the optical property is absorbance of light at a preselected wavelength or transmittance of light at a preselected wavelength.

5. The method of claim 1, wherein in step (b)(i), the optical property is turbidity.

6. The method of claim 1, wherein in step (b)(ii), the optical property is absorbance of light at a preselected wavelength or transmittance of light at a preselected wavelength.

7. The method of claim 1, wherein in step (b)(ii), the optical property is turbidity.

8. The method of claim 1, wherein in step (a), the hemocyte preparation is an amebocyte lysate.

9. The method of claim 8, wherein the amebocyte lysate is a *Limulus* amebocyte lysate.

10. The method of claim 1, wherein step (a) is performed in a cartridge.

11. The method of claim 1, wherein step (a) is performed in a well defined by a solid support.

12. The method of claim 1, wherein in step (a), the mixture further comprises a chromogenic moiety or a fluorogenic moiety.

13. The method of claim 12, wherein the chromogenic moiety comprises a para-nitroaniline chromophore.

14. The method of claim 12, wherein the chromogenic substrate moiety comprises Ile-Glu-Ala-Arg-pNA (SEQ ID NO: 1), where pNA is a para-nitroaniline group.

15. The method of claim 1, wherein one or more of the standard values is a range of values of the optical property.

16. The method of claim 1, wherein one or more of the standard values is a range of times in which a preselected change occurs in the optical property.

* * * * *

SEQUENCE LISTING

```
<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Chemically Synthesized

<400> SEQUENCE: 1

Ile Glu Ala Arg
1
```